US012590052B2

(12) United States Patent
Zhang et al.

(10) Patent No.: US 12,590,052 B2
(45) Date of Patent: Mar. 31, 2026

(54) COMPOSITE MATERIAL, METHOD FOR PREPARING THE SAME, AND LIGHT-EMITTING DIODE

(71) Applicant: TCL TECHNOLOGY GROUP CORPORATION, Huizhou (CN)

(72) Inventors: Xuanyu Zhang, Huizhou (CN); Zhiwen Nie, Huizhou (CN); Wenyong Liu, Huizhou (CN)

(73) Assignee: TCL TECHNOLOGY GROUP CORPORATION, Huizhou (CN)

( * ) Notice: Subject to any disclaimer, the term of this patent is extended or adjusted under 35 U.S.C. 154(b) by 914 days.

(21) Appl. No.: 17/840,103

(22) Filed: Jun. 14, 2022

(65) Prior Publication Data

US 2022/0310954 A1 Sep. 29, 2022

Related U.S. Application Data

(63) Continuation of application No. PCT/CN2020/139300, filed on Dec. 25, 2020.

(30) Foreign Application Priority Data

Jun. 9, 2020 (CN) ......................... 202010519784.4

(51) Int. Cl.
*C07C 63/331* (2006.01)
*B82Y 20/00* (2011.01)
(Continued)

(52) U.S. Cl.
CPC .......... *C07C 63/331* (2013.01); *C07C 211/54* (2013.01); *C07C 323/62* (2013.01);
(Continued)

(58) Field of Classification Search
CPC ......... B82Y 20/00; B82Y 30/00; B82Y 40/00; C07C 63/331; C07C 211/54; C07C 323/62; H10K 50/115
(Continued)

(56) References Cited

U.S. PATENT DOCUMENTS

| | | | | |
|---|---|---|---|---|
| 2013/0204025 A1* | 8/2013 | Buso | ...................... | C07F 3/003 556/130 |
| 2018/0366651 A1 | 12/2018 | Kim et al. | | |
| 2019/0288230 A1 | 9/2019 | Kim et al. | | |

FOREIGN PATENT DOCUMENTS

| | | |
|---|---|---|
| CN | 107603340 A | 1/2018 |
| CN | 108735906 A1 | 11/2018 |

(Continued)

OTHER PUBLICATIONS

Koh "Coordination Copolymerization Mediated by Zn4O(CO2R)6 Metal Clusters: a Balancing Act between Statistics and Geometry." JACS 2010, 132, 42, 15005-15010 (Year: 2010).*

(Continued)

*Primary Examiner* — Tri V Nguyen
(74) *Attorney, Agent, or Firm* — Maier & Maier, PLLC

(57) ABSTRACT

A method for preparing a composite material, including the following steps: providing metal oxide nanoparticles and a polyaromatic compound having a structure represented by Formula I, Formula I (Continued)

where, $Ar_1$, $Ar_2$, $Ar_3$, and $Ar_4$ are selected from aromatic rings; $X_1$, $X_2$, and $X_3$ are selected from active groups configured for binding with the metal oxide nanoparticles, each of $R_1$, $R_2$, and $R_3$ independently contains at least one of alkylene, amine, —N═N—, alkenyl, alkynyl, and phenyl, and each of m, n, and y is independently selected from 0 or positive integers; dispersing the polyaromatic compound and the metal oxide nanoparticles in a solvent to yield a mixed solution; and heating the mixed solution to yield the composite material. A composite material includes: a polyaromatic compound and metal oxide nanoparticles. The polyaromatic compound is connected to the metal oxide nanoparticles. The polyaromatic compound has a structure represented by Formula I.

17 Claims, 2 Drawing Sheets

(51) Int. Cl.

| | |
|---|---|
| ***B82Y 30/00*** | (2011.01) |
| ***B82Y 40/00*** | (2011.01) |
| ***C07C 211/54*** | (2006.01) |
| ***C07C 323/62*** | (2006.01) |
| ***H10K 50/115*** | (2023.01) |
| ***H10K 85/00*** | (2023.01) |
| ***H10K 102/00*** | (2023.01) |
| ***H10K 102/10*** | (2023.01) |

(52) U.S. Cl.
CPC ........... *H10K 50/115* (2023.02); *B82Y 20/00* (2013.01); *B82Y 30/00* (2013.01); *B82Y 40/00* (2013.01); *H10K 85/00* (2023.02); *H10K 2102/00* (2023.02); *H10K 2102/102* (2023.02); *H10K 2102/351* (2023.02); *H10K 2102/361* (2023.02)

(58) Field of Classification Search
USPC ........................................................ 252/519.2
See application file for complete search history.

(56) References Cited

FOREIGN PATENT DOCUMENTS

| | | | |
|---|---|---|---|
| CN | 109935714 | A | 6/2019 |
| CN | 110518123 | A | 11/2019 |
| CN | 110718637 | A | 1/2020 |

OTHER PUBLICATIONS

Zhu "MOF-templated syntheses of porous Co304 hollow spheres and micro-flowers for enhanced performance in supercapacitors." CrystEngComm, 2018, 20, 3812 (Year: 2018).*
Mikhalyova "CeO2 Nanoparticle Sensitization of Eu3+-Centered Luminescence in a Composite CeO2/Eu3+-MOF". Theoretical and Experimental Chemistry, vol. 52, No. 5, Nov. 2016 (Year: 2016).*
Li "Shape-controlled synthesis and lithium-storage study of metal-organic frameworks Zn40(1,3,5-benzenetribenzoate)2". Journal of Power Sources 160 (2006) 542-547 (Year: 2006).*
International Search Report mailed Mar. 24, 2021, in corresponding to International Application No. PCT/CN2020/139300; 6 pages.

* cited by examiner providing metal oxide nanoparticles and a polyaromatic compound having a structure represented by Formula I:

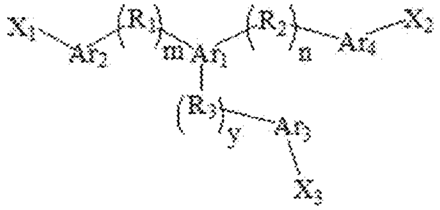

(I), in which, $Ar_1$, $Ar_2$, $Ar_3$, and $Ar_4$ are selected from aromatic rings; $X_1$, $X_2$, and $X_3$ are selected from active groups configured for binding with the metal oxide nanoparticles; each of $R_1$, $R_2$, and $R_3$ independently contains at least one of alkylene, amine, -N=N-, alkenyl, alkynyl, and phenyl; and each of m, n, and y is independently selected from 0 or positive integers;

↓ dispersing the polyaromatic compound and the metal oxide nanoparticles in a solvent to yield a mixed solution; and

↓ heating the mixed solution to yield the composite material.

FIG. 1

COMPOSITE MATERIAL, METHOD FOR PREPARING THE SAME, AND LIGHT-EMITTING DIODE

CROSS-REFERENCE TO RELATED APPLICATIONS

This application is a continuation application of International Patent Application No. PCT/CN2020/139300 with an international filing date of Dec. 25, 2020, designating the United States, now pending, and further claims priority benefits to Chinese Patent Application No. 202010519784.4 filed Jun. 9, 2020 The contents of all of the aforementioned applications, including any intervening amendments thereto, are incorporated herein by reference.

TECHNICAL FIELD

The present application relates to the field of the display technology, and more particularly to a composite material, a method for preparing the same, and a light-emitting diode.

BACKGROUND

A typical method for preparing a quantum dot light-emitting diode (QLED) device usually adopts a solution method to prepare an electronic functional layer, for example, metal oxide nanoparticles, such as ZnO, are adopted as the electron transport layer (ETL) of the QLED device and spin-coated onto a quantum dot light-emitting layer. However, such method has the following defects: 1) in order to maintain the excellent optical stability of quantum dots, the surface ligands of quantum dots are non-polar, thus having poor contact with ZnO and making electron injection difficult; 2) since the electron mobility of existing QLED devices is much higher than the hole mobility, this makes the charge accumulation at the QD/ETL interface very serious, and results a very adverse effect on the efficiency and lifespan of the QLED device; and 3) the existing film structure formed by spin-coating ZnO nanoparticles often shows a disordered loose structure and has poor quality of the electron transport layer and various defects, such as micropores and the like, and the poor film-forming performance.

SUMMARY

In order to solve the above technical problems, embodiments of the present application adopt the following technical solutions:

In a first aspect, a method for preparing a composite material is provided. The method comprises the following steps:

providing metal oxide nanoparticles and a polyaromatic compound having a structure represented by Formula I:

Formula I

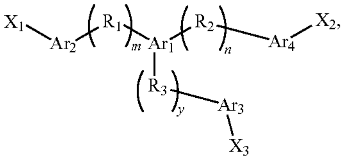

in which, $Ar_1$, $Ar_2$, $Ar_3$, and $Ar_4$ are selected from aromatic rings; $X_1$, $X_2$, and $X_3$ are selected from active groups configured for binding with the metal oxide nanoparticles; each of $R_1$, $R_2$, and $R_3$ independently contains at least one of alkylene, amine, —N═N—, alkenyl, alkynyl, and phenyl; and each of m, n, and y is independently selected from 0 or positive integers;

dispersing the polyaromatic compound and the metal oxide nanoparticles in a solvent to yield a mixed solution; and heating the mixed solution to yield the composite material.

In a second aspect, a composite material is provided. The composite material comprises: a polyaromatic compound and metal oxide nanoparticles. The polyaromatic compound is connected to the metal oxide nanoparticles.

The polyaromatic compound has a structure represented by Formula I:

Formula I

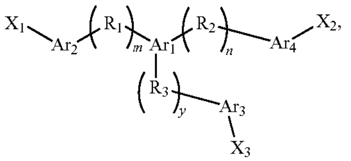

in which, $Ar_1$, $Ar_2$, $Ar_3$, and $Ar_4$ are selected from aromatic rings; $X_1$, $X_2$, and $X_3$ are selected from active groups configured for binding with the metal oxide nanoparticles; each of $R_1$, $R_2$, and $R_3$ independently contains at least one of alkylene, amine, —N═N—, alkenyl, alkynyl, and phenyl; and each of m, n, and y is independently selected from 0 or positive integers.

In a third aspect, a light-emitting diode is provided. The light-emitting diode comprises:

an anode and a cathode that are oppositely arranged;

a light-emitting layer, arranged between the anode and the cathode; and an electronic functional layer, arranged between the cathode and the light-emitting layer.

A material of the electronic functional layer comprises: the composite material prepared by the above-described preparation method, or the above-described composite material.

The light-emitting diode provided by embodiments of the present application includes the electronic functional layer which is prepared by the above preparation method, thus having high brightness, long life, and excellent luminous performance.

BRIEF DESCRIPTION OF THE DRAWINGS

In order to illustrate the technical solutions in embodiments of the present application more clearly, accompanying drawings that are used in the description of the embodiments or exemplary technologies are briefly introduced hereinbelow. Obviously, the drawings in the following description are only some embodiments of the present application. For those skilled in the art, other drawings can also be obtained according to these drawings without any creative effort.

FIG. 1 is a flowchart of a method for preparing a composite material provided by embodiments of the present application;

DETAILED DESCRIPTION OF THE EMBODIMENTS

Figure 2:
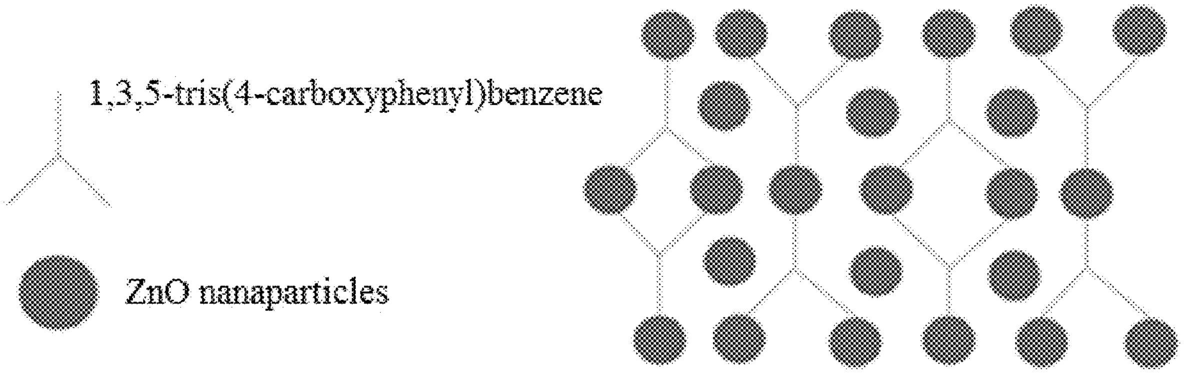
FIG. 2 is a schematic diagram of a microstructure of a composite material prepared by the preparation method provided by embodiments of the present application.

In order to make the purposes, technical solutions, and advantages of the present application clearer and more understandable, the present application will be further described in detail hereinafter with reference to the accompanying drawings and embodiments. It should be understood that the embodiments described herein are only intended to illustrate but not to limit the present application.

As shown in FIG. 1, embodiments of the present application provide a method for preparing a composite material. The method comprises the following steps:

S01, providing metal oxide nanoparticles and a polyaromatic compound having a structure represented by Formula I:

Formula I

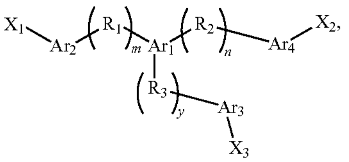

in which, $Ar_1$, $Ar_2$, $Ar_3$, and $Ar_4$ are selected from aromatic rings; $X_1$, $X_2$, and $X_3$ are selected from active groups configured for binding with the metal oxide nanoparticles; each of $R_1$, $R_2$, and $R_3$ independently contains at least one of alkylene, amine, —N═N—, alkenyl, alkynyl, and phenyl; and each of m, n, and y is independently selected from 0 or positive integers;

S02, dispersing the polyaromatic compound and the metal oxide nanoparticles in a solvent to yield a mixed solution; and S03, heating the mixed solution to yield the composite material.

In the preparation method of the composite material, the polyaromatic compound having the structure represented by Formula I is adopted as a dopant material, when the polyaromatic compound and the metal oxide nanoparticles are mixed and heated, active groups are coordinately bonded to metal ions on surfaces of the metal oxide nanoparticles, such that the polyaromatic compound and the metal oxide nanoparticles are crosslinked to form a three-dimensional network structure. In the meanwhile, as the polyaromatic compound has a planar triangular structure, the metal oxide nanoparticles are arranged in an orderly manner during film formation to form a layered superlattice structure, and those zinc oxide nanoparticles not connected to the polyaromatic compound are filled in the micropores of the structure, thus, film property and crystalline property of the metal oxide film are effectively improved. In another aspect, as the metal oxide nanoparticles are doped with the above polyaromatic compound, the polyaromatic compound effectively occupies oxygen vacancies on the surfaces of metal oxide nanoparticles through active groups, which reduces the formation energy of oxygen vacancies to a certain extent, promotes the probability of the detachment of oxygen atoms from surfaces of the metal oxide nanoparticles to form vacancies, increases the concentration of oxygen vacancies, and in turn effectively reduces the resistance of the composite material, thereby being beneficial to improve the resistance transmission performance of the material. In still another aspect, by doping the polyaromatic compound into the composite material, the polarity of the mixed solution is adjusted, and the interface contact performance between the metal oxide nanoparticles and the quantum dots light-emitting layer is improved, which is beneficial to further improve the surface property of the material, and to enhance the electron injection. The composite material prepared by the above preparation method has an ordered material structure, high density, and few surface defects, which is beneficial to improve the conduction and recombination ability of electrons at the interface, enhance electron injection, reduce the charge accumulation at the QD/ETL interface, and effectively balance the hole injection rate and the electron injection rate of the device, thereby comprehensively improving the brightness and lifespan of the light-emitting device.

Specifically, in step S01 the polyaromatic compound has a molecular structure represented by Formula I:

Formula I

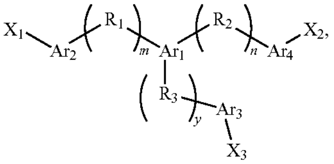

in which, $Ar_1$, $Ar_2$, $Ar_3$, and $Ar_4$ are selected from aromatic rings. In the specification of the present application, "aromatic rings" refers to a class of planar ring systems having a conjugated structure, including benzene rings and fused rings, and the like. The fused rings include but are not limited to naphthalene rings, anthracene rings, phenanthrene rings, and the like. Meanwhile, the benzene ring can optionally be selected from a substituted benzene ring or an unsubstituted benzene ring. In some embodiments, $Ar_1$, $Ar_2$, $Ar_3$ and $Ar_4$ are selected from benzene rings.

$X_1$, $X_2$, and $X_3$ are selected from active groups capable of binding with the metal oxide nanoparticles. By coordinately bond the active groups to the metal atoms on the surfaces of the metal oxide nanoparticles, a plurality of metal oxide nanoparticles and a plurality of the polyaromatic compounds are crosslinked to form the composite material having the layered superlattice structure, which promotes the metal oxide nanoparticles to have an orderly arrangement during the film formation, and improves the film property and the crystalline property of the metal oxide film. In some embodiments, each of $X_1$, $X_2$, and $X_3$ is independently at least one of selected from hydroxyl, carboxyl, sulfhydryl, and amino.

Each of $R_1$, $R_2$, and $R_3$ independently contains at least one of alkylene, amine, —N═N—, alkenyl, alkynyl, and phenyl. Each of m, n, and y is independently selected from 0 or positive integers.

In the specification of the present application, "alkylene" is a class of organic groups containing only carbon and hydrogen atoms, which can be linear, branched, or cyclic, including but not limited to methylene, ethylene, isopropylidene, n-pentylene, and the like. "Amine" is a class of N-containing organic groups, to which at most one hydrogen atom is attached, including but not limited to —NH—, —$N(CH_3)$—, —$N(CH_2CH_3)$—, and the like. "Alkenyl" is a hydrocarbon group containing at least one carbon-carbon double bond, including but not limited to vinyl, propenyl, allyl, and the like. “Alkynyl” is a hydrocarbon group containing at least one carbon-carbon triple bond, including but not limited to ethynyl, propynyl, and the like.

In some embodiments, each of $R_1$, $R_2$, and $R_3$ is independently at least one selected from the group consisting of alkylene, amine, —N═N—, alkenyl, alkynyl, and phenyl. The center of the polyaromatic compound is formed with a large conjugated π bond, which has a hyperconjugation effect and is beneficial to improve the electronic conductivity of the composite material. In the meanwhile, the polyaromatic compound has a highly rigid planar structure, which improves the crystallinity of the composite material having a layered superlattice structure to a certain extent, thereby further improving the film property and the crystalline property of the metal oxide film. Moreover, the polyaromatic compound has a stable planar triangular structure, and the polyaromatic compound and metal oxide nanoparticles are assembled to form the layered superlattice structure, which is isotropic and has the same chemical potential in all directions of space, thus facilitating the metal oxide nanoparticles to combine with the active groups in all directions in an orderly manner, and in turn forming a composite material having stable crystal structure and stable properties.

Each of m, n, and y is independently selected from 0 or positive integers. When m, n, and y are all 0, $Ar_1$ is directly connected with $Ar_2$, $Ar_3$, and $Ar_4$ via carbon-carbon single bonds. When m, n, and y are not 0, $Ar_1$ is connected with $Ar_2$, $Ar_3$, and $Ar_4$ via the connection groups $R_1$, $R_2$, $R_3$, and the like. When m, n, and y are selected from positive integers, such integers are preferably between 1 and 3, for example, m, n, and y can be all 1; or alternatively, m is 2, both n and y are 1; or alternatively, m is 1, n is 2, and y is 3.

In some embodiments, each of m, n, and y is independently selected from 0 or 1. For example, m, n, and y are all selected to be 0 or 1; or alternatively, m is 0, and both n and y are selected to be 1; or alternatively, both m and y are selected to be 1, and n is 0. In this way, the polyaromatic compound has a certain conjugation effect to ensure that the composite material has a certain electronic conductivity, and in the meanwhile, it is ensured that the polyaromatic compound is bound with the metal oxide nanoparticles to form a layered superlattice structure.

On the basis of the above embodiments, the polyaromatic compound is any one or more compounds selected from the group consisting of

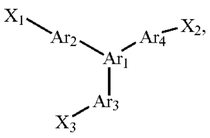
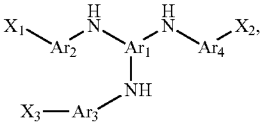
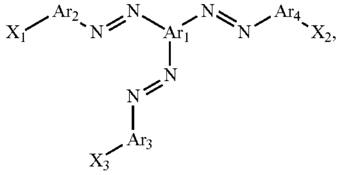
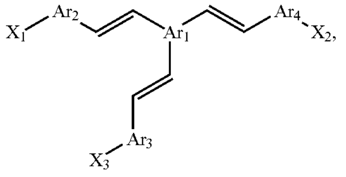

-continued

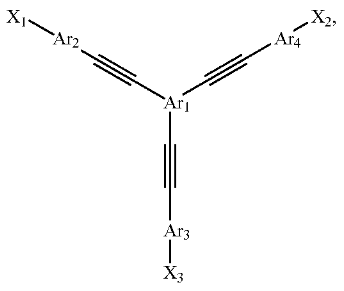

and

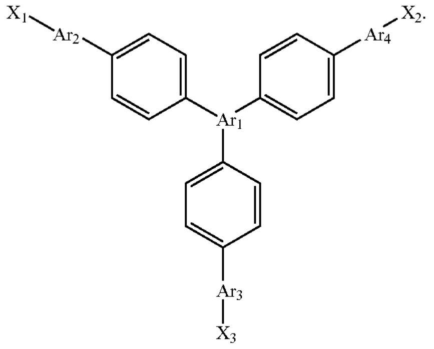

In a further embodiment, the polyaromatic compound is any one selected from the group consisting of:

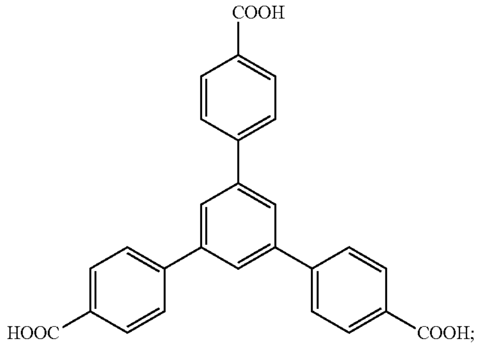

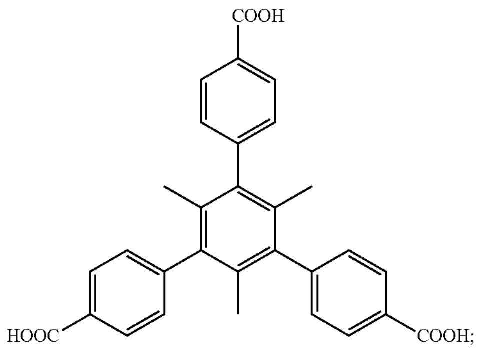

-continued

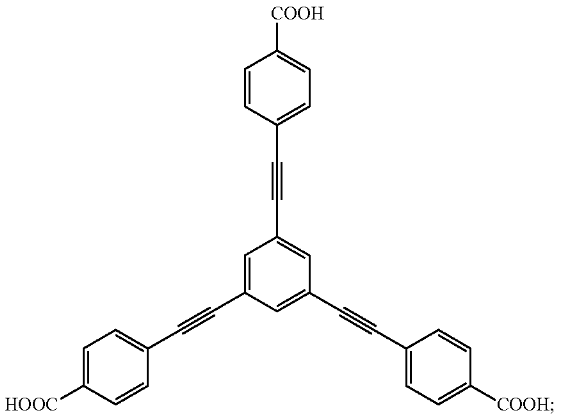

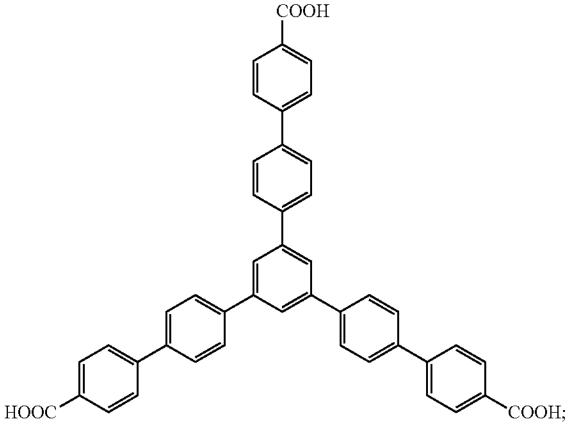

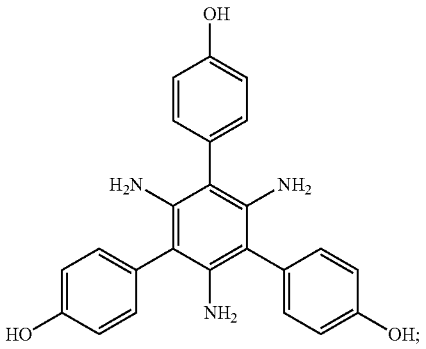

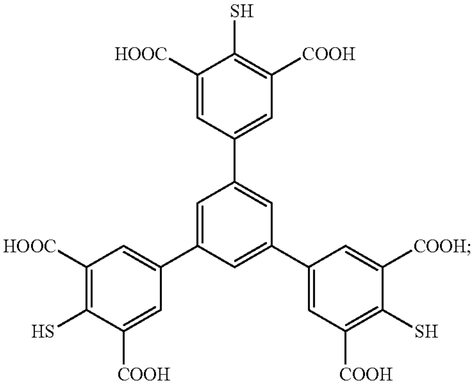

-continued

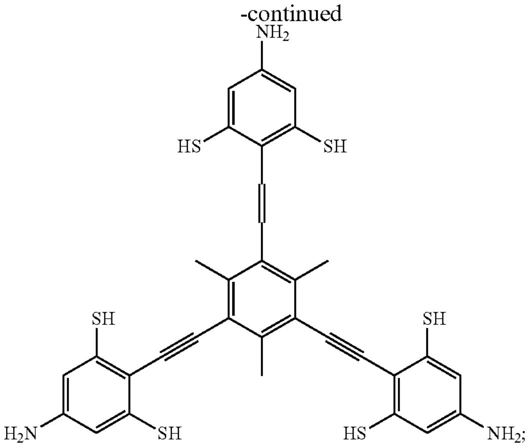

and

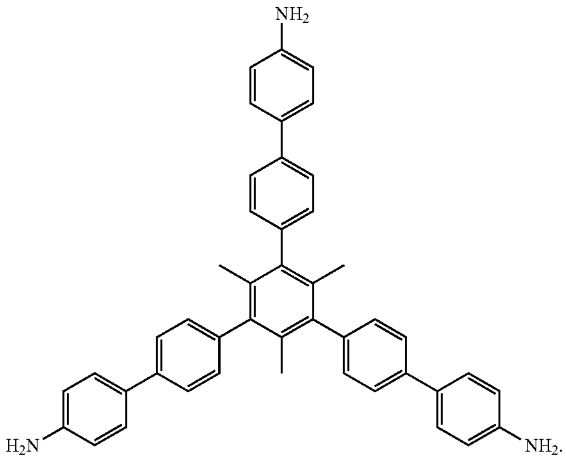

The polyaromatic compounds as listed in the above all have a highly symmetrical planar structure, and charge centers thereof are all concentrated on the benzene ring in the middle, which has a strong conjugation effect, and the range of hyperconjugation effect formed after coordinative bonding with the metal oxide nanoparticles is sufficient to connect charge centers of different molecules, so that electrons can jump on different charge centers, which greatly enhances the carrier transport performance of the composite material. Meanwhile, all the above polyaromatic compounds have a triangular structure and excellent stability, no matter from which direction the external electric potential or chemical potential attacks, and the consistent stability can be ensured, such polyaromatic compound has no easy-to-attack site.

In a specific embodiment, the polyaromatic compound is any one compound selected from the group consisting of:

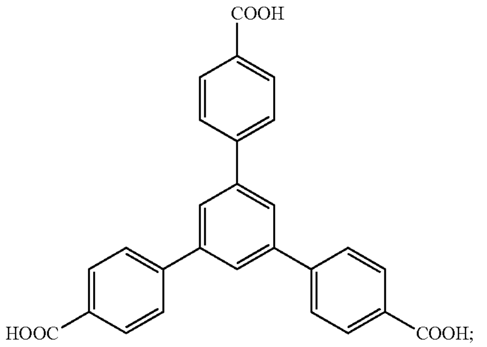

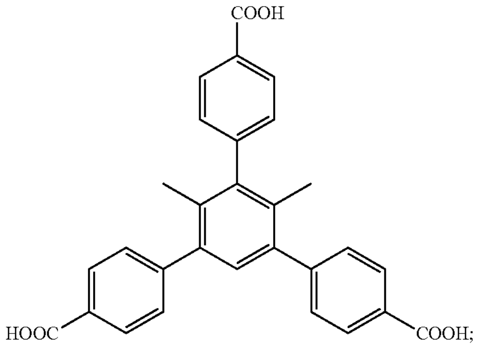

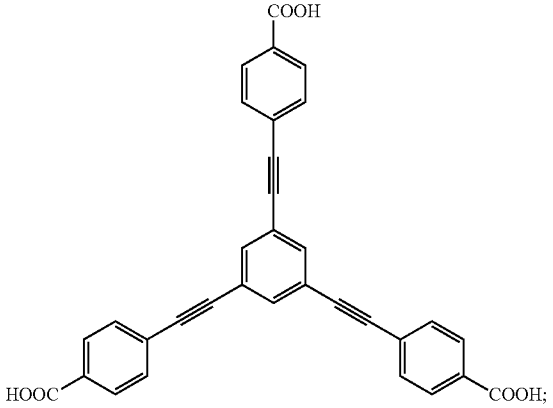

and

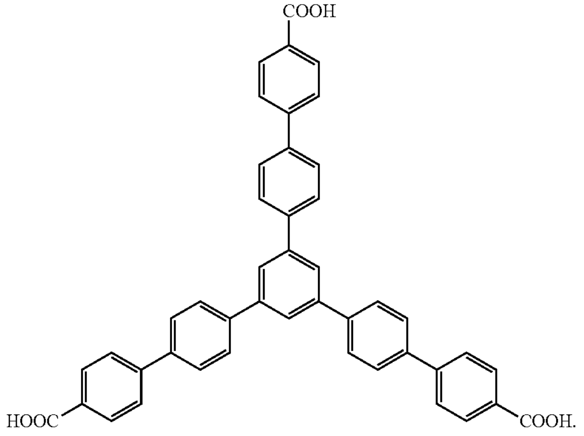

As the functional material of the composite material, the metal oxide nanoparticles are selected from n-type semiconductor nanoparticles for the preparation of the electronic functional layer in light-emitting diodes. Preferably, the metal oxide nanoparticles comprise zinc oxide nanoparticles and/or indium tin oxide nanoparticles. In some embodiments, the metal oxide nanoparticles are selected from the zinc oxide nanoparticles, which have high electron mobility and wide band gap, and positions of conduction band and valence band thereof are more suitable in light-emitting diode structure. In a further embodiment, sizes of the zinc oxide nanoparticles are between 4 and 5 nm. The zinc oxide nanoparticles having such a size range have good dispersion performance in corresponding solvent, and match the sizes (about 2 nm) of the polyaromatic compound ligands selected in the above, which is beneficial to improve the production efficiency of composite materials.

In step S02, the polyaromatic compound and metal oxide nanoparticles are respectively dispersed in the solvent, so that the polyaromatic compound and the metal oxide nanoparticles are fully mixed and contact with each other in the solution.

In some embodiments, the step of dispersing the polyaromatic compound and the metal oxide nanoparticles in the solvent comprises:

S021, dispersing the metal oxide nanoparticles in the solvent to obtain a first solution;

S022, dispersing the polyaromatic compound in the solvent to obtain a second solution; and S023, mixing the first solution and the second solution.

By dissolving the metal oxide nanoparticles and the polyaromatic compound respectively in the solvent, and mixing resulting solutions, complete and uniform mixing of the polyaromatic compound and the metal oxide nanoparticles can be facilitated, thus a clear mixed solution can be obtained.

For the specific operation of dissolving metal oxide nanoparticles in the solvent, reference can be made to conventional techniques in the art, for example, mechanical stirring, ultrasound method, and the like are adopted to dissolve metal oxide nanoparticles in the solvent to form a clear metal oxide solution. The operation of dissolving the polyaromatic compound in the solvent adopts the same methods.

The solvent is used as the reaction medium for preparing the above composite materials, and can be selected from common organic solvents in the art, including but not limited to alkanes, alkenes, alcohols, ethers, aromatic compounds, and the like, which does not affect the assembly of metal oxide nanoparticles and the polyaromatic compound, and which are easy to evaporate. Preferably, the solvent is selected from a polar or moderately polar solvent. The quantum dot materials of the light-emitting layer in the existing light-emitting diode are mainly oil-phase quantum dots. When preparing the light-emitting diode, the polyaromatic compound and metal oxide nanoparticles are dissolved in the polar or moderately polar solvent to form the mixed solution, the polarity of which is orthogonal with the polarity of the quantum dots, thus preventing the solvent from eroding the light-emitting layer and from causing the structure of the light-emitting layer to be damaged. In some embodiments, the solvent is selected from at least one of ethanol, propanol, butanol, and pentanol.

In the step of dispersing the polyaromatic compound and metal oxide nanoparticles in the solvent, the film property of the prepared composite material can be controlled by adjusting the relative amounts of the polyaromatic compound and metal oxide nanoparticles.

In some embodiments, a molar ratio of the polyaromatic compound to the metal oxide nanoparticles in the mixed solution is (1-5):30, and addition amounts of the polyaromatic compound and the metal oxide nanoparticles are controlled within the above molar ratio range, so and to enable the composite material to have excellent film properties. Taking zinc oxide nanoparticles and 1,3,5-tris(4-carboxyphenyl)benzene as an example, as shown in FIG. 2, 1,3,5-tris(4-carboxyphenyl)benzene is coordinately bond with part of the zinc oxide nanoparticles through carboxyl at a terminal of 1,3,5-tris(4-carboxyphenyl)benzene, thereby crosslinking each other and forming a network structure, while remaining zinc oxide nanoparticles are filled in the micropores of the network structure, thereby reducing the microporous defects of the zinc oxide film and improving the crystallinity and density of the zinc oxide film. When the molar ratio of the polyaromatic compound to the metal oxide nanoparticles is smaller than 1:30, the doping amount of the polyaromatic compound is too small to improve the film property and the crystalline property of the material; and when the molar ratio of the polyaromatic compound to the metal oxide nanoparticles is greater than 5:30, the doping amount of the polyaromatic compound is too large, which easily leads to the increase of microporous defects in the material film.

In step S03, in the process of heating the mixed solution, the polyaromatic compound and the metal oxide nanoparticles are assembled to form a layered superlattice structure similar to MOFs, and the solvent is volatilized, which promotes the metal oxide nanoparticles to form a film having an orderly arrangement, thereby obtaining an organic-inorganic type composite material.

As an implementation manner, in the step of heating the mixed solution, the heating temperature is between 80 and 140° C., and the heating duration is between 30 min and 2 hrs. When the temperature is lower than 80° C., the minimum activation energy requirement for the crystallization of the composite material cannot be achieved; and when the temperature is higher than 140° C., the structural stability of the metal oxide nanoparticles is easily affected. Meanwhile, within such heating temperature range, when the heating duration is shorter than 40 min, the crystallization process of the composite material cannot be completed; when the heating duration is longer than 2 hrs, the structure of the metal oxide nanoparticles will be adversely affected.

As an implementation manner, in the step of heating the mixed solution, the mixed solution is firstly deposited on a substrate and then the heat treatment is performed. The substrate acts as a carrier for the deposition of mixed solution to facilitate the formation of composite film. The type and structure of the substrate may refer to conventional techniques in the art, and may be a glass plate, or a glass plate having a functional film layer formed on a surface thereof.

In a specific embodiment, in the step of heating the mixed solution, the mixed solution is deposited on the substrate, and heated at a temperature of 80° C.-140° C. for between 30 min and 2 hrs.

In summary, under the combined effect of the above-mentioned preferred raw materials, optimized process conditions, and parameters, the final composite material has excellent film property and crystalline property, which effectively solves the problem that the existing film structure formed by spin-coating metal oxide nanoparticles often shows a disordered loose structure and has poor quality of the electron transport layer, and which effectively improves the conduction and recombination ability of electrons at the interface, enhances electron injection, reduces the charge accumulation at the QD/ETL interface, and effectively balances the hole and electron injection rates of the device, thereby comprehensively improving the brightness and lifespan of the light-emitting device.

On the basis of the above technical solutions, embodiments of the present application further provide a composite material and a light-emitting diode.

Correspondingly, the composite material comprises: a polyaromatic compound and metal oxide nanoparticles. The polyaromatic compound is connected to the metal oxide nanoparticles.

The polyaromatic compound has a structure represented by Formula I:

Formula I

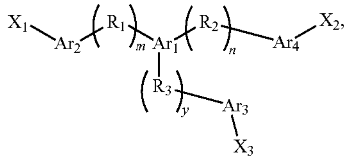

in which, $Ar_1$, $Ar_2$, $Ar_3$, and $Ar_4$ are selected from aromatic rings; $X_1$, $X_2$, and $X_3$ are selected from active groups configured for binding with the metal oxide nanoparticles; each of $R_1$, $R_2$, and $R_3$ independently contains at least one of alkylene, amine, —N═N—, alkenyl, alkynyl, and phenyl; and each of m, n, and y is independently selected from 0 or positive integers.

The composite material provided by the embodiment of the present application is prepared by the above-mentioned preparation method, includes the polyaromatic compound and the metal oxide nanoparticles cross-linked with each other, and has an orderly structure, high density, few surface defects, excellent surface property, thereby being beneficial for improving the brightness and lifespan of light-emitting devices.

The composite material prepared by the above preparation method provided in embodiments of the present application preferably exists in the form of a film, and has an orderly structure, high density, few surface defects, and excellent surface property of the material.

In some embodiments, $Ar_1$, $Ar_2$, $Ar_3$, and $Ar_4$ are selected from benzene rings; and/or each of $X_1$, $X_2$, and $X_3$ is any one independently selected from the group consisting of hydroxyl, carboxyl, sulfhydryl, and amino; and/or each of $R_1$, $R_2$, and $R_3$ is independently at least one selected from the group consisting of alkylene, amine, —N═N—, alkenyl, alkynyl, and phenyl; and/or each of m, n, and y is independently selected from 0 or 1.

In some embodiments, the polyaromatic compound is at least one selected from the group consisting of:

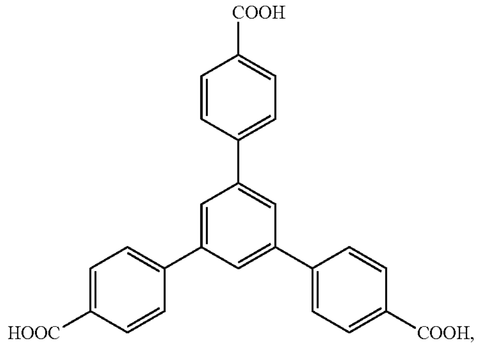

-continued

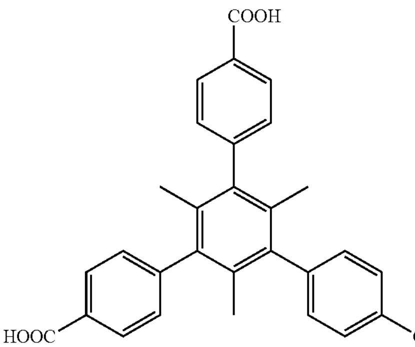,

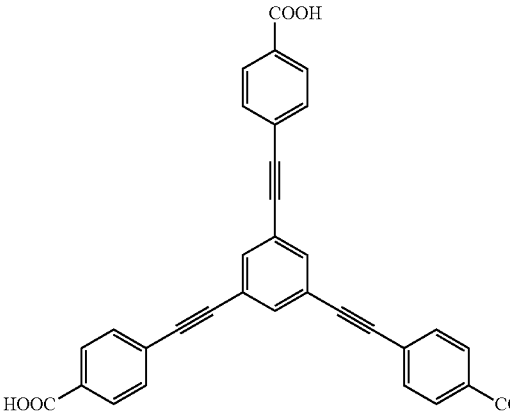,

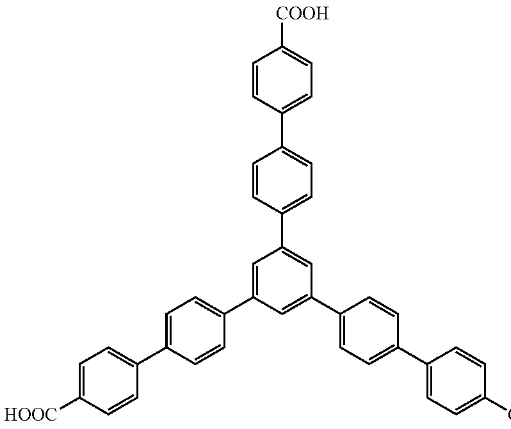,

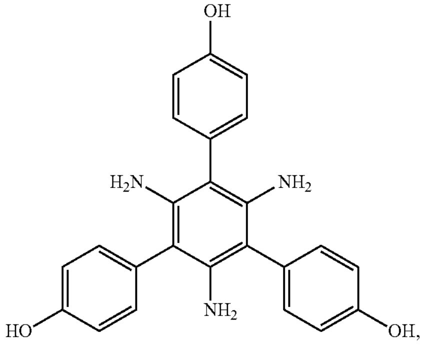,

-continued

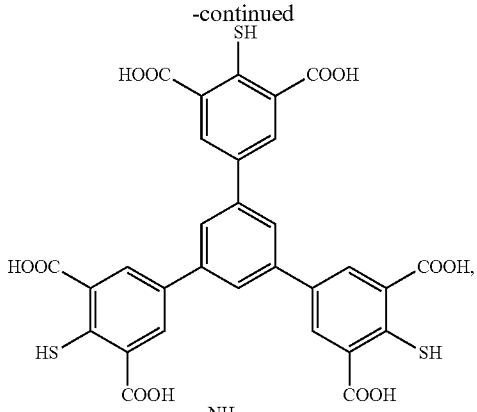,

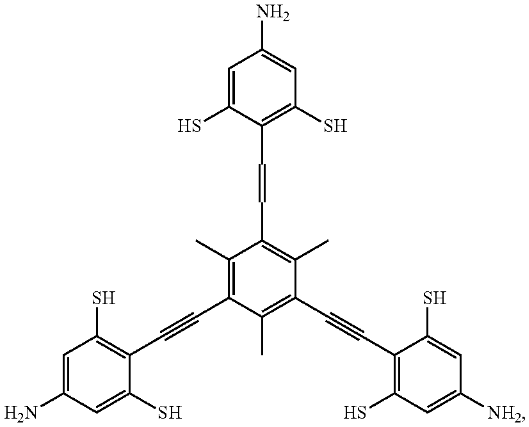, and

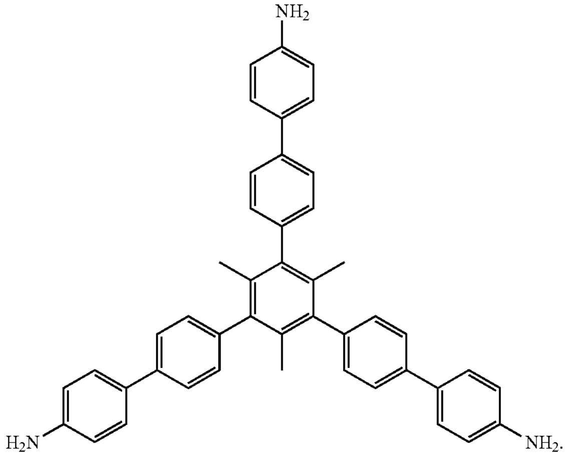.

In some embodiments, the metal oxide nanoparticles comprise zinc oxide nanoparticles and/or zinc tin oxide nanoparticles; and/or a molar ratio of the polyaromatic compound to the metal oxide nanoparticles in the mixed solution is (1-5):30.

In a specific embodiment, the composite material is formed by compositing the above-described polyaromatic compound and the above-described metal oxide nanoparticles.

Figure 3:
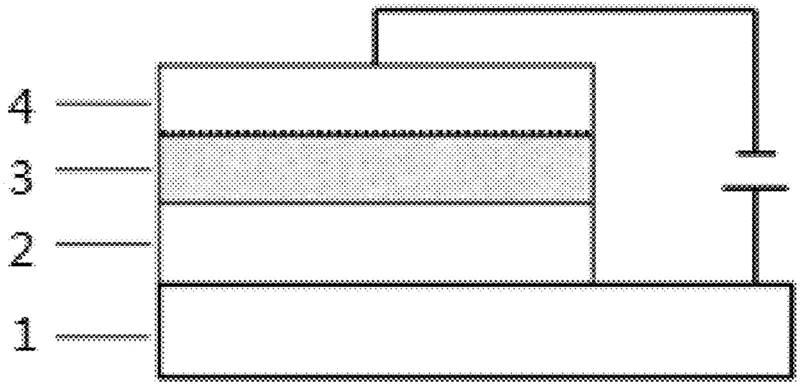
FIG. 3 is a schematic diagram of a light-emitting diode provided by embodiments of the present application.

Correspondingly, as shown in FIG. 3, embodiments of the present application provide a light-emitting diode. The light-emitting diode comprises: an anode 1, a light-emitting layer 2, an electronic functional layer 3, and a cathode 4. The anode 1 and the cathode 4 are oppositely arranged. The light-emitting layer 2 is arranged between the anode 1 and the cathode 4. The electronic functional layer 3 is arranged between the light-emitting layer 2 and the cathode 4. A material of the electronic functional layer 3 comprises: a composite material prepared by the preparation method as described in the above, or the composite material as described in the above.

The light-emitting diode provided by embodiments of the present application includes the electronic functional layer which is prepared by the above preparation method, thus having high brightness, long life, and excellent luminous performance.

In some embodiments, the material for electronic functional layer is the above composite material. Specifically, the composite material is composited of the polyaromatic compound and the metal oxide nanoparticles.

A molar ratio of the polyaromatic compound to the metal oxide nanoparticles is (1-5):30.

The metal oxide nanoparticles comprise zinc oxide nanoparticles and/or zinc tin oxide nanoparticles.

The polyaromatic compound comprises at least one of the following compounds:

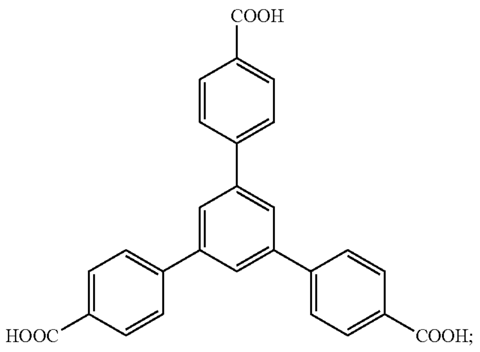

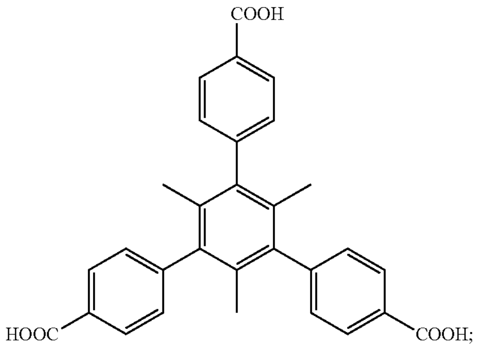

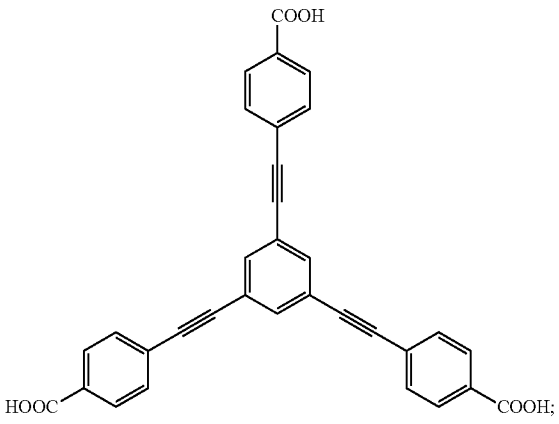

-continued

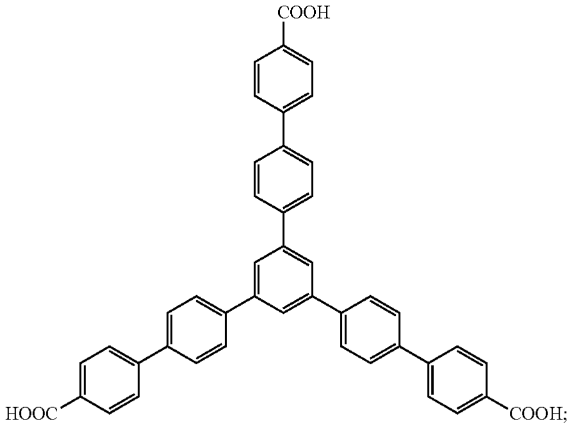

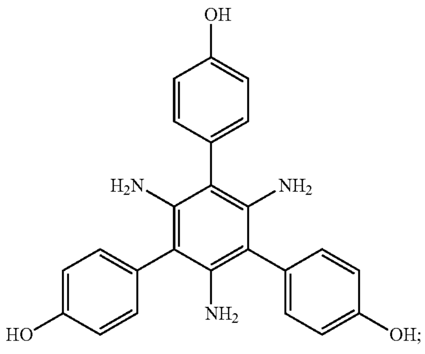

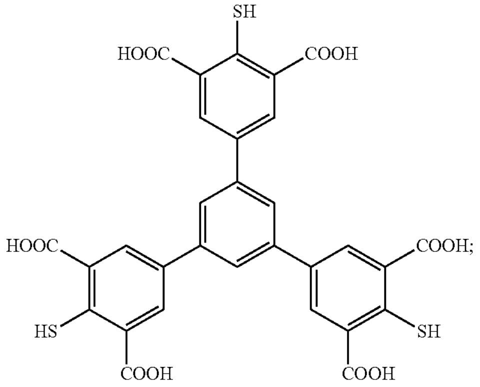

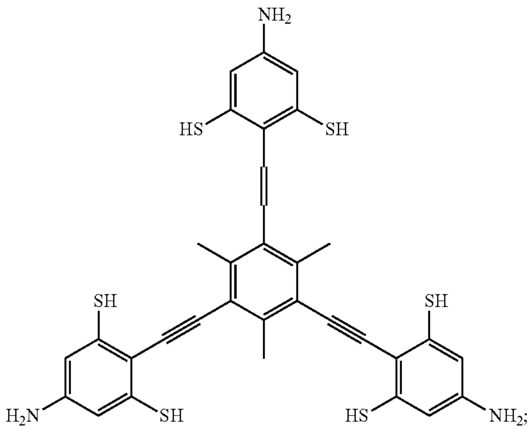

and

-continued

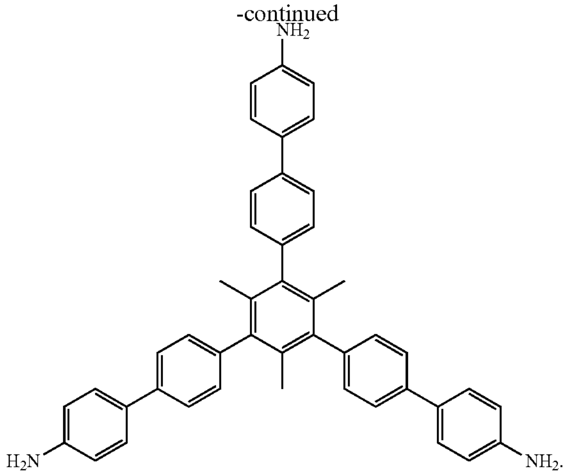

The electronic functional layer generally refers to an electron injection layer, an electron transport layer, and an electron blocking layer. In some embodiments, the electronic functional layer is an electron transport layer. In a specific embodiment, a thickness of the electronic functional layer is between 10 and 180 nanometers.

The structure of the light-emitting diode can refer to conventional techniques in the art. In some embodiments, the light-emitting diode is an upright structure, and the anode is connected to the substrate as a bottom electrode. In other embodiments, the light-emitting diode is an inverted structure, and the cathode is connected to the substrate as the bottom electrode. Further, in addition to the above-mentioned basic functional membrane layers such as the cathode, the anode, the electronic functional layer, and the light-emitting layer, between the anode and the light-emitting layer are further arranged hole functional layers, such as the hole injection layer, the hole transport layer, and the hole blocking layer.

In some embodiments, the light-emitting diode includes: the anode, the hole injection layer, the hole transport layer, the light-emitting layer, the electron transport layer, and the cathode which are stacked in sequence. The anode is connected to the substrate to form a bottom. The electron transport layer is prepared by the above preparation method.

A thickness of the bottom electrode is 20-200 nm; a thickness of the hole injection layer is 20-200 nm; a thickness of the hole transport layer is 30-180 nm; a total thickness of the light-emitting layer is 30-180 nm; a thickness of the electron transport layer is 10-180 nm; and a thickness of the cathode is 40-190 nm.

Optionally, the substrate can be a rigid substrate or a flexible substrate, including but not limited to a glass, a silicon wafer, and the like.

Optionally, the anode can be a conductive metal oxide, including but not limited to zinc oxide, indium oxide, tin oxide, indium tin oxide (ITO), and the like.

Optionally, the hole injection layer can be polythiophene, $WoO_3$, or the like.

Optionally, the hole transport layer can be TFB, TPD, or the like.

Optionally, the light-emitting layer material can be II-VI groups such as CdS, III-V groups such as GaN, or IV-VI groups such as SnS.

Optionally, the cathode can be a metal or an alloy, including but not limited to aluminum, silver, and the like.

When preparing the above-mentioned light-emitting diode, the anode, the hole injection layer, the hole transport layer, the light-emitting layer, the electron transport layer and the cathode are sequentially formed on the substrate by adopting magnetron sputtering, chemical vapor deposition, evaporation, spin coating, inkjet printing, and other methods.

As an implementation manner, a method for preparing a QLED device, comprises:

(1) forming an anode on a substrate;
(2) forming a hole injection layer on the anode;
(3) forming a hole transport layer on the hole injection layer;
(4) depositing a light-emitting layer on the hole transport layer;
(5) depositing an electron transport layer on the light-emitting layer; and
(6) forming a cathode layer on the electron transport layer.

In order to illustrate the technical solutions provided by the present application, the following detailed description is given in conjunction with specific examples.

Example 1

This example provides a light-emitting diode, which was prepared as follows:

(1) an anode was formed on a substrate;
(2) PEDOT: PSS was spin-coated on the anode to form a hole injection layer;
(3) TFB was spin-coated on the hole injection layer at 3000 r/min for 30 s, and heated at 150° C. for 30 min to form a hole transport layer;
(4) CdZnSe/ZnSe quantum dots were spin-coated on the hole transport layer at 3000 r/min for 30 s and then annealed to form a light-emitting layer;
(5) a ZnO-ethanol solution was added and dissolved into a 1,3,5-tris(4-carboxyphenyl)benzene-ethanol solution at room temperature to form a clear mixed solution according to a molar ratio of 1,3,5-tris(4-carboxyphenyl)benzene to ZnO of 1:30, and the resulting mixed solution was spin-coated on the light-emitting layer at 3000 r/min for 30 s, and heated at 150° C. for 30 min to form an electron transport layer;
(6) A1 electrodes were evaporated on the electron transport layer, and encapsulated with an electronic glue, to obtain a QLED device.

Herein, 1,3,5-tris(4-carboxyphenyl)benzene ha a molecular structure of

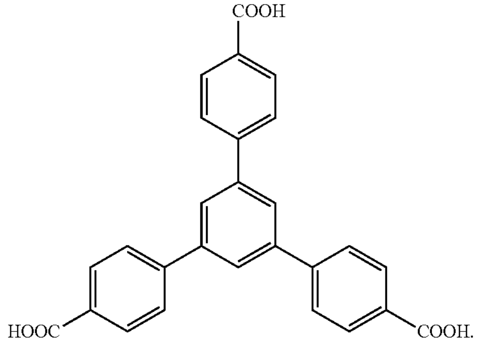 [SMILES: O=C(O)c1ccc(-c2cc(-c3ccc(C(=O)O)cc3)cc(-c3ccc(C(=O)O)cc3)c2)cc1]

Comparative Example 1

This comparative example provides a light-emitting diode, which was prepared by substantially the same method as Example 1, except that in step (5), it was ZnO-ethanol solution that was spin-coated on the light-emitting layer.

Example 2

This example provides a light-emitting diode, which was prepared as follows:

(1) an anode was formed on a substrate;

(2) PEDOT: PSS was spin-coated on the anode to form a hole injection layer;

(3) TFB was spin-coated on the hole injection layer, and heated at 150° C. for 30 min to form a hole transport layer;

(4) CdZnSe/ZnSe/ZnS quantum dots were sprayed on the hole transport layer to form a light-emitting layer;

(5) a ZnO-ethanol solution was added and dissolved into a 1,3,5-trimethyl-2,4,6-tris(4-carboxyphenyl)benzene-ethanol solution at room temperature to form a clear mixed solution according to a molar ratio of 1,3,5-trimethyl-2,4,6-tris(4-carboxyphenyl)benzene to ZnO of 2:30, and the resulting mixed solution was sprayed on the light-emitting layer, and heated at 80° C. for 30 min to form an electron transport layer;

(6) A1 electrodes were evaporated on the electron transport layer, and encapsulated with an electronic glue, to obtain a QLED device.

Herein, 1,3,5-trimethyl-2,4,6-tris(4-carboxyphenyl)benzene has a molecular structure of

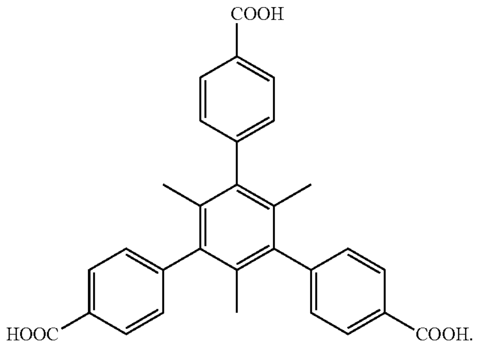 [SMILES: Cc1c(-c2ccc(C(=O)O)cc2)c(C)c(-c2ccc(C(=O)O)cc2)c(C)c1-c1ccc(C(=O)O)cc1]

Comparative Example 2

This comparative example provides a light-emitting diode, which was prepared by substantially the same method as Example 2, except that in step (5), it was ZnO-ethanol solution that was spin-coated on the light-emitting layer.

Example 3

This example provides a light-emitting diode, which was prepared as follows:

(1) an anode was formed on a substrate;

(2) PEDOT: PSS was spin-coated on the anode to form a hole injection layer;

(3) TFB was spin-coated on the hole injection layer, and heated at 150° C. for 30 min to form a hole transport layer;

(4) CdZnSe/ZnSe/CdZnS quantum dots were spin-coated on the hole transport layer to form a light-emitting layer;

(5) a ZnO-ethanol solution was added and dissolved into a 1,3,5-trimethyl-2,4,6-tris(4-carboxyphenyl)benzene-ethanol solution at room temperature to form a clear mixed solution according to a molar ratio of 1,3,5-trimethyl-2,4,6-tris(4-carboxyphenyl)benzene to ZnO of 1.5:30, and the resulting mixed solution was deposited on the light-emitting layer, and heated at 80° C. for 30 min to form an electron transport layer;

(6) A1 electrodes were evaporated on the electron transport layer, and encapsulated with an electronic glue, to obtain a QLED device.

Herein, 1,3,5-tris(4-carboxyphenylethynyl)benzene has a molecular structure of

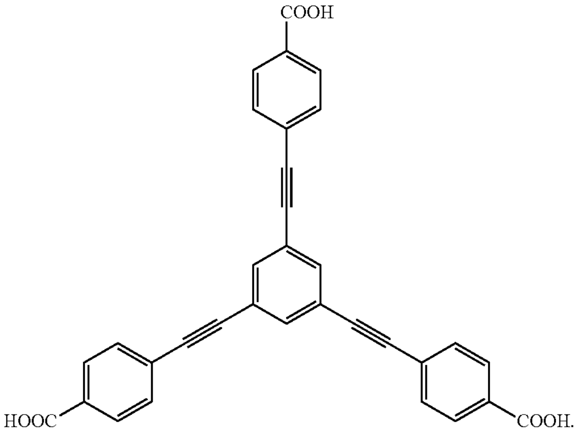 [SMILES: O=C(O)c1ccc(C#Cc2cc(C#Cc3ccc(C(=O)O)cc3)cc(C#Cc3ccc(C(=O)O)cc3)c2)cc1]

Comparative Example 3

This comparative example provides a light-emitting diode, which was prepared by substantially the same method as Example 3, except that in step (5), it was ZnO-ethanol solution that was spin-coated on the light-emitting layer.

Example 4

This example provides a light-emitting diode, which was prepared as follows:

(1) an anode was formed on a substrate;

(2) PEDOT: PSS was spin-coated on the anode to form a hole injection layer;

(3) TFB was spin-coated on the hole injection layer, and heated at 150° C. for 30 min to form a hole transport layer;

(4) CdZnSeS/ZnS quantum dots were spin-coated on the hole transport layer at 4000 r/min for 30 s, and then annealed to form a light-emitting layer;

(5) a ZnO-ethanol solution was added and dissolved into a 1,3,5-tris(4'-carboxy[1,1'-biphenyl]-4-yl)benzene-ethanol solution at room temperature to form a clear mixed solution according to a molar ratio of 1,3,5-tris (4'-carboxy[1,1'-biphenyl]-4-yl)benzene to ZnO of 3:30, and the resulting mixed solution was spin-coated on the light-emitting layer at 3000 r/min for 30 s, and heated at 80° C. for 30 min to form an electron transport layer;

(6) A1 electrodes were evaporated on the electron transport layer, and encapsulated with an electronic glue, to obtain a QLED device.

Herein, 1,3,5-tris(4'-carboxy[1,1'-biphenyl]-4-yl)benzene has a molecular structure of

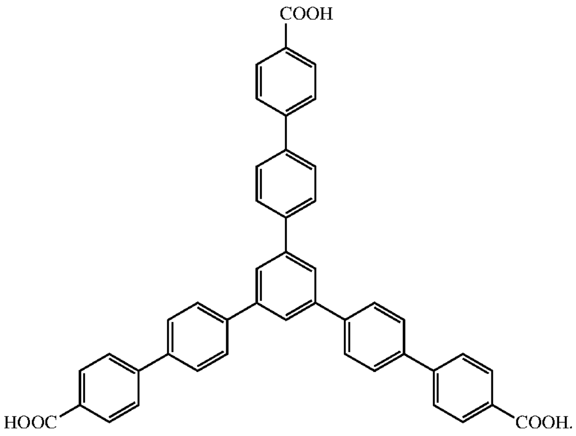 [SMILES: O=C(O)c1ccc(-c2ccc(-c3cc(-c4ccc(-c5ccc(C(=O)O)cc5)cc4)cc(-c4ccc(-c5ccc(C(=O)O)cc5)cc4)c3)cc2)cc1]

Comparative Example 4

This comparative example provides a light-emitting diode, which was prepared by substantially the same method as Example 4, except that in step (5), it was ZnO-ethanol solution that was spin-coated on the light-emitting layer.

Example 5

This example provides a light-emitting diode, which was prepared by substantially the same method as Example 1, except that in step (5), the ZnO nanoparticles were replaced by zinc tin oxide nanoparticles.

Light-emitting diodes prepared by Example 1-5 and Comparative Example 1-4 were performed with performance tests. The test indicators and test methods are as follows:

(1) External Quantum Efficiency (EQE)

A ratio of the number of outgoing photons converted from the number of electron-hole pairs injected into the quantum dots, with a unit of %, is an important parameter to measure the quality of electroluminescent devices, and can be obtained by EQE optical testing instrument. The specific calculation formula is as follows:

$$EQE = \eta_e \eta_r \chi \frac{K_R}{K_R + K_{NR}}$$

in which, $\eta_e$ is an optical outcoupling efficiency, $\eta_r$ is a ratio of the number of recombined carriers to the number of injected carriers, $\chi$ is the ratio of the number of excitons producing photons to the total number of excitons, $K_R$ is a radiation process rate, $K_{NR}$ is a nonradiative process rate.

Test conditions included: room temperature, and 30-60% of the air humidity.

(2) Lifespan of the QLED device: the device was driven by a constant current or voltage, and the time required for the brightness to decrease to a certain proportion of the maximum brightness was tested. Herein, the time required for the brightness to decrease to 95% of the maximum brightness was defined as T95, and the lifespan was the measured lifespan. In order to shorten the test cycle, the lifespan test of the device was usually carried out by accelerating the aging of the device under high brightness with reference to the OLED device test, and the lifespan under high brightness was obtained by fitting the extended exponential decay brightness decay fitting formula, such as: Lifespan at 1000 nits was defined as T951000 nit. The specific calculation was as follows:

$$T95_L = T95_H \cdot \left(\frac{L_H}{L_L}\right)^A$$

In the formula, $T95_L$ was the lifespan under a low brightness, $T95_H$ was a measured lifespan under a high brightness, $L_H$ was the acceleration of the device to the highest brightness, $L_L$ was 1000 nit, and A was the acceleration factor. For OLED, the value of A was usually 1.6-2. In this experiment, the A value was 1.7 by measuring the lifespan of several groups of green QLED devices at rated brightness.

A lifespan test system was adopted to carry out the lifespan test of the corresponding devices. The test conditions included: room temperature, and 30-60% of the air humidity.

The test results are shown in Table 3 below: both EQE and lifespan of the light-emitting diodes provided by Examples 1-5 are higher than the corresponding comparative examples.

TABLE 1

| | $EQE_{max}$ | $T95_{1000\ nit}$ | | $EQE_{max}$ | $T95_{1000\ nit}$ |
|---|---|---|---|---|---|
| Example 1 | 2.0% | 18.90 h | Comparative Example 1 | 1.2% | 10.32 h |
| Example 2 | 2.1% | 16.21 h | Comparative Example 2 | 1.8% | 14.76 h |
| Example 3 | 2.5% | 10.73 h | Comparative Example 3 | 2.1% | 7.21 h |
| Example 4 | 2.4% | 9.56 h | Comparative Example 4 | 1.9% | 7.10 h |
| Example 5 | 3.2% | 30.27 h | | | |

The above are only optional embodiments of the present application, and are not intended to limit the present application. Various modifications and variations of the present application are possible for those skilled in the art. Any modification, equivalent replacement, improvement, etc. made within the spirit and principle of the present application shall be included within the scope of the claims of the present application.

What is claimed is:

1. A composite material, consisting of: a polyaromatic compound and metal oxide nanoparticles;

wherein the polyaromatic compound and a part of the metal oxide nanoparticles are crosslinked to form a network structure having micropores, and a remaining part of the metal oxide nanoparticles fill in micropores of the network structure; and the polyaromatic compound has a structure represented by Formula I:

(I)

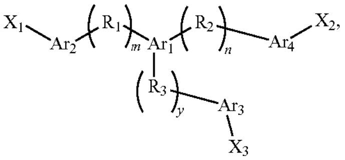

in which, $Ar_1$, $Ar_2$, $Ar_3$, and $Ar_4$ are selected from aromatic rings; $X_1$, $X_2$, and $X_3$ are selected from active groups configured for binding with the metal oxide nanoparticles; each of $R_1$, $R_2$, and $R_3$ independently contains at least one of alkylene, amine, —N═N—, alkenyl, alkynyl, and phenyl; and each of m, n, and y is independently selected from 0 or positive integers; and a molar ratio of the polyaromatic compound to the metal oxide nanoparticles is (1-5):30.

2. The composite material of claim 1, wherein $Ar_1$, $Ar_2$, $Ar_3$, and $Ar_4$ are selected from benzene rings; and/or each of $X_1$, $X_2$, and $X_3$ is any one independently selected from the group consisting of hydroxyl, carboxyl, sulfhydryl, and amino; and/or each of $R_1$, $R_2$, and $R_3$ is independently at least one selected from the group consisting of alkylene, amine, —N═N—, alkenyl, alkynyl, and phenyl; and/or each of m, n, and y is independently selected from 0 or 1.

3. The composite material of claim 2, wherein the polyaromatic compound comprises at least one of the following compounds:

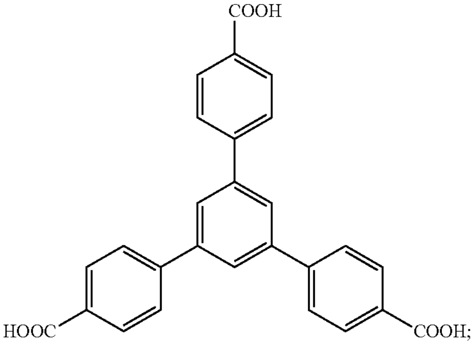

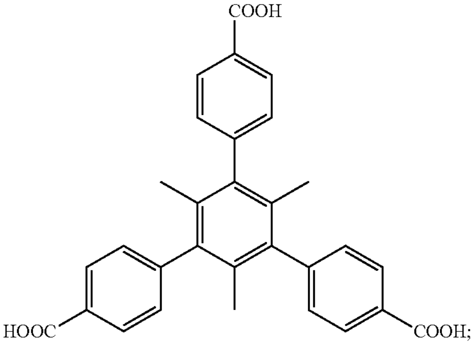

-continued

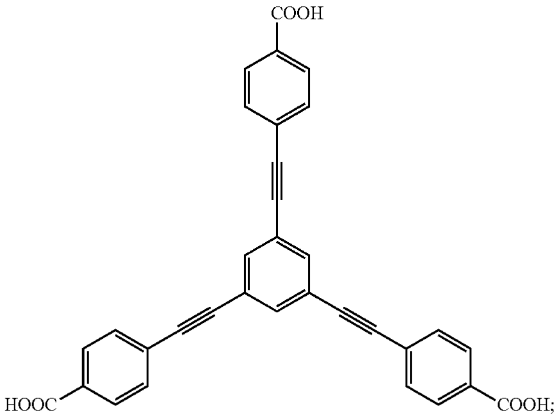

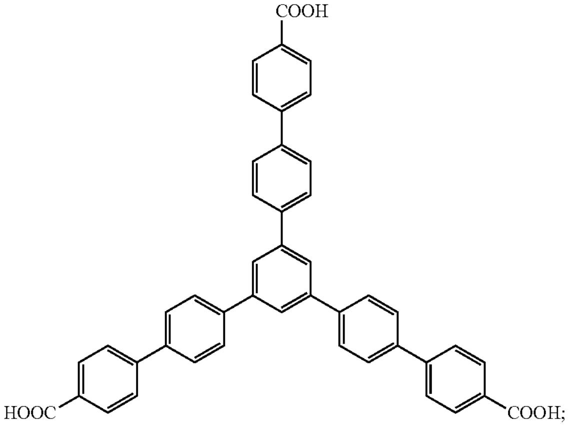

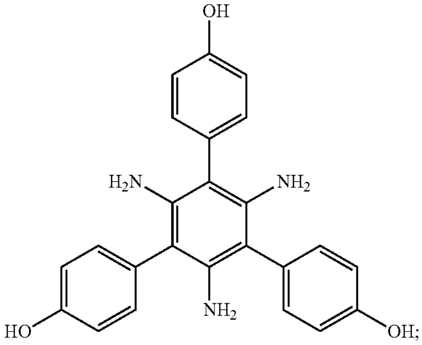

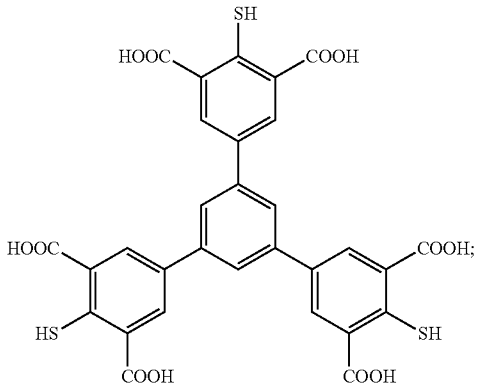

-continued

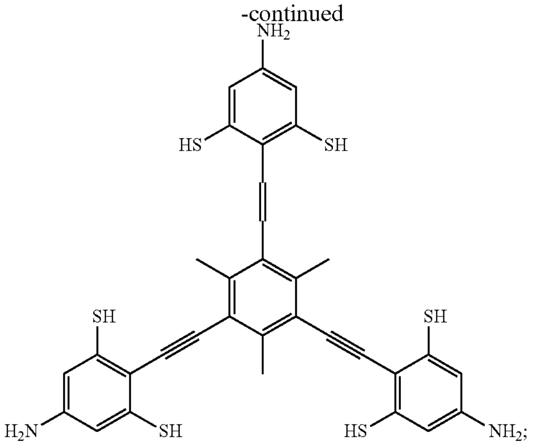

and

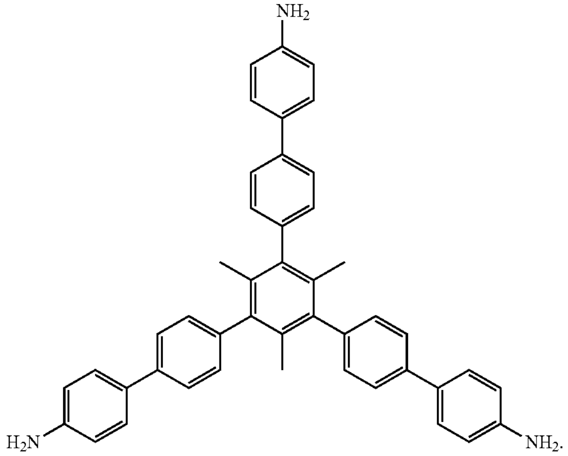

4. The composite material of claim 1, wherein
the metal oxide nanoparticles comprise zinc oxide nanoparticles and/or zinc tin oxide nanoparticles.

5. The composite material of claim 1, wherein the composite material is formed by compositing the polyaromatic compound and the metal oxide nanoparticles.

6. A light-emitting diode, comprising:
an anode and a cathode that are oppositely arranged;
a light-emitting layer, arranged between the anode and the cathode; and
an electronic functional layer, arranged between the cathode and the light-emitting layer, and comprising the composite material of claim 1.

7. The light-emitting diode according to claim 6, wherein
the electronic functional layer is an electron transport layer; and/or
a thickness of the electronic functional layer is between 10 and 180 nanometers.

8. A method for preparing the composite material of claim 1, the method comprising the following steps:
providing the metal oxide nanoparticles and the polyaromatic compound;
dispersing the polyaromatic compound and the metal oxide nanoparticles in a solvent to yield a mixed solution; and
heating the mixed solution to yield the composite material.

9. The method of claim 8, wherein in the step of heating the mixed solution, a heating temperature is between 80 and 140° C., and a heating duration is between 30 min and 2 hrs.

10. The method of claim 8, wherein the step of heating the mixed solution comprises: depositing the mixed solution on a substrate, and performing heating treatment.

11. The method of claim 8, wherein the polyaromatic compound is any one or more compounds selected from the group consisting of

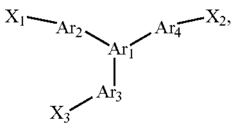

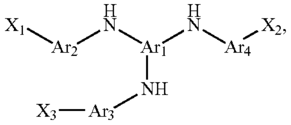

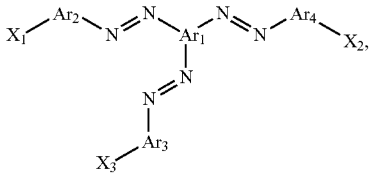

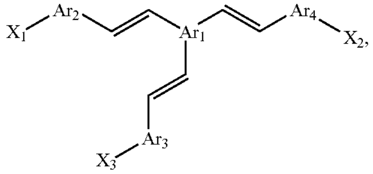

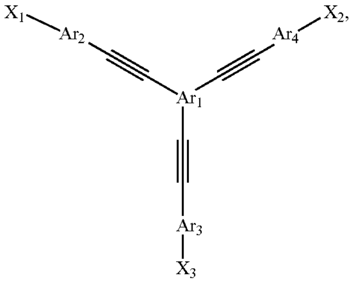

and

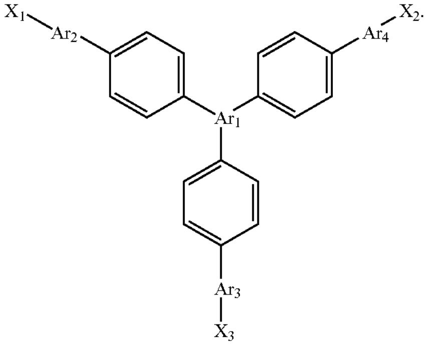

12. The method of claim 11, wherein
$Ar_1$, $Ar_2$, $Ar_3$, and $Ar_4$ are selected from benzene rings; or
each of $X_1$, $X_2$, and $X_3$ is any one independently selected from the group consisting of hydroxyl, carboxyl, sulfhydryl, and amino.

13. The method of claim 11, wherein
$Ar_1$, $Ar_2$, $Ar_3$, and $Ar_4$ are selected from benzene rings; and
each of $X_1$, $X_2$, and $X_3$ is any one independently selected from the group consisting of hydroxyl, carboxyl, sulfhydryl, and amino.

14. The method of claim 13, wherein the polyaromatic compound is at least one selected from the group consisting of:
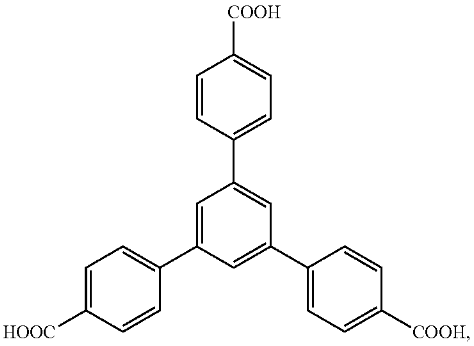
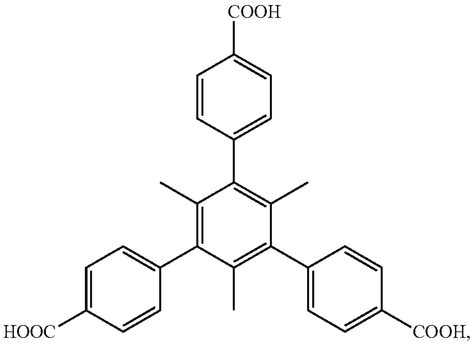
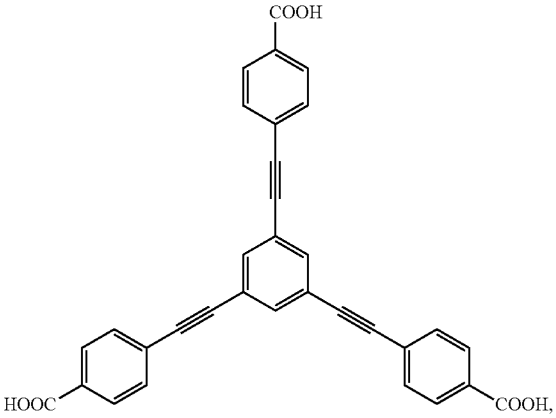
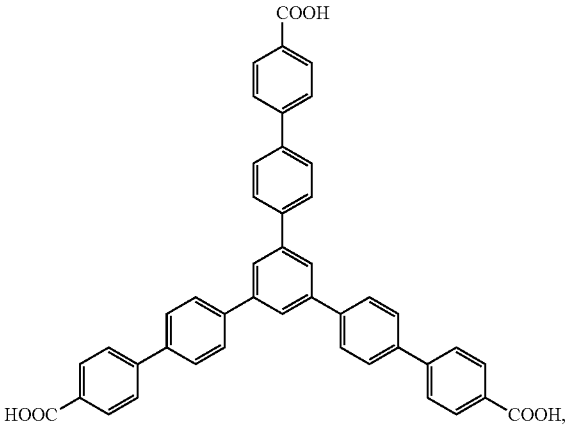
-continued
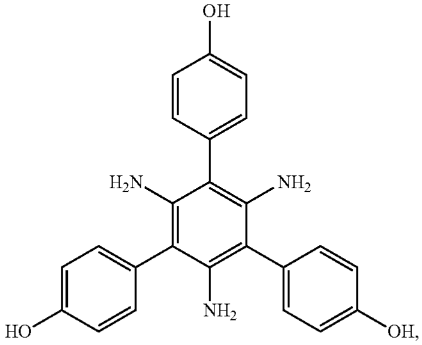
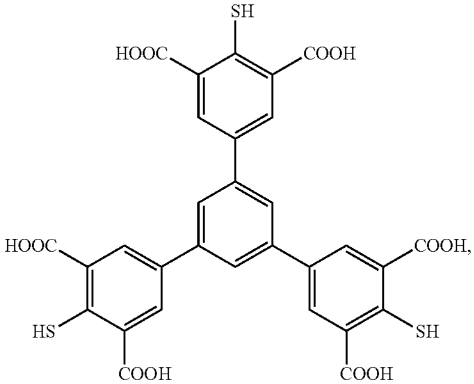
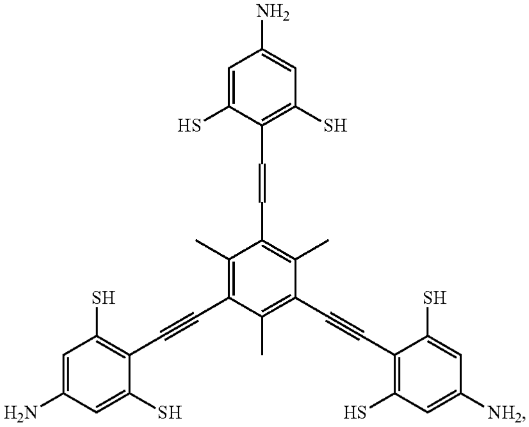
and
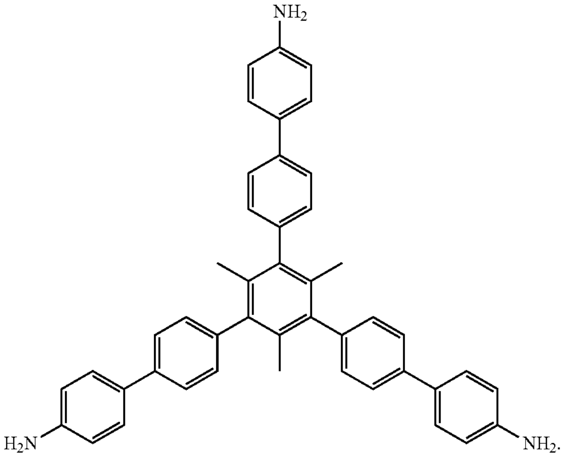
15. The method of claim 8, wherein the metal oxide nanoparticles comprise zinc oxide nanoparticles and/or zinc tin oxide nanoparticles.

16. The method of claim 8, wherein the solvent is any one selected from the group consisting of ethanol, propanol, butanol, and pentanol.

17. The method of claim 8, wherein the step of dispersing the polyaromatic compound and the metal oxide nanoparticles in the solvent comprises:

dispersing the metal oxide nanoparticles in the solvent to obtain a first solution;

dispersing the polyaromatic compound in the solvent to obtain a second solution; and mixing the first solution and the second solution.

* * * * *